US006196222B1

(12) United States Patent
Heinonen et al.

(10) Patent No.: US 6,196,222 B1
(45) Date of Patent: *Mar. 6, 2001

(54) TRACHEAL GAS INSUFFLATION DELIVERY SYSTEM FOR RESPIRATION EQUIPMENT

(75) Inventors: Erkki P. O. Heinonen, Helsinki (FI); Lars Å Larsson, Järfalla (SE)

(73) Assignee: Instrumentarium Corporation, Helsinki (FI)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/037,483

(22) Filed: Mar. 10, 1998

(51) Int. Cl.[7] .............................. A61M 16/00; A62B 7/00; F16K 31/02

(52) U.S. Cl. ............................... 128/204.23; 128/204.18; 128/204.21

(58) Field of Search ................... 128/204.18, 204.21, 128/204.23, 204.24, 204.28, 207.14, 207.16; 604/23, 26

(56) References Cited

U.S. PATENT DOCUMENTS

| 4,617,924 | 10/1986 | Heim et al. ..................... 128/204.23 |
|---|---|---|
| 4,627,860 | * 12/1986 | Rowland ......................... 128/204.22 |
| 4,632,107 | * 12/1986 | Butler ............................. 128/204.24 |
| 4,648,395 | * 3/1987 | Sato et al. ....................... 128/204.23 |
| 4,674,495 | * 6/1987 | Orr ................................. 128/207.14 |
| 4,681,099 | * 7/1987 | Sato et al. ....................... 128/204.23 |
| 4,686,974 | * 8/1987 | Sato et al. ....................... 128/204.23 |
| 4,702,241 | 10/1987 | Gravenstein et al. .......... 128/204.25 |
| 4,770,168 | 9/1988 | Rusz et al. ..................... 128/203.12 |

(List continued on next page.)

FOREIGN PATENT DOCUMENTS

| 1 122 630 | 10/1984 | (EP). |
|---|---|---|
| 0 659 445 | 6/1995 | (EP). |
| WO 09/14852 | 12/1990 | (WO). |
| WO 92/20394 | 11/1992 | (WO). |
| 97/31670 | 2/1996 | (WO). |
| WO 97/31670 | * 9/1997 | (WO) .............................. 128/204.23 |

OTHER PUBLICATIONS

Tracheal Gas Insufflation during Pressure–control Ventilation: Effect of Catheter Position, Diameter & Flow Rate. Nahum et al., American Review of Respiratory Diseases (vol. 146, pp. 1411–1418), Jul. 1992.*

Tracheal Gas Insufflation as an Adjunct to Ventilation, John J. Marini; Current Opinion in Anaesthesiology 1995; 8:545–550; Rapid Science Publishers ISSN 0952–7907.

Primary Examiner—John G. Weiss
Assistant Examiner—Joseph F. Weiss, Jr.
(74) Attorney, Agent, or Firm—Andrus, Sceales, Starke, & Sawall, LLP (57) ABSTRACT

A tracheal gas insufflation delivery system for use with a ventilator breathing system including a ventilator and a breathing circuit. The delivery system includes a flow generator connected to the inspiratory limb of the breathing circuit through an inlet line. The flow generator is operated to draw off a supply of gas to be used during tracheal gas insulation through the inlet line. The flow generator is connected by a delivery line to the patient limb of the breathing circuit, preferably, near the distal end of an endotracheal tube used in the patient limb. The gas supplied by the delivery line reduces the volume of previously exhaled gases subsequently breathed by the patient increasing the physiological efficiency of patient ventilation and allowing a reduction in ventilatory pressures. The tracheal gas insufflation delivery system may include an intermediate cylinder that can be filled by the flow generator so that the tracheal gas insufflation delivery system can deliver a greater supply of gas.

30 Claims, 4 Drawing Sheets

U.S. PATENT DOCUMENTS

| | | | | |
|---|---|---|---|---|
| 4,850,371 | * | 7/1989 | Broadhurst et al. | 128/207.14 |
| 4,966,141 | * | 10/1990 | Bacaner et al. | 128/207.14 |
| 5,043,576 | * | 8/1991 | Broadhurst et al. | 250/293 |
| 5,048,515 | * | 9/1991 | Sanso | 128/204.26 |
| 5,239,994 | | 8/1993 | Atkins | 128/204.18 |
| 5,255,675 | * | 10/1993 | Kolobow | 128/204.18 |
| 5,419,314 | * | 5/1995 | Christopher | 128/200.26 |
| 5,423,313 | * | 6/1995 | Olsson et al. | 128/204.21 |
| 5,471,977 | * | 12/1995 | Olsson et al. | 128/204.22 |
| 5,531,218 | * | 7/1996 | Krebs | 128/203.12 |
| 5,626,131 | * | 5/1997 | Chua et al. | 128/204.23 |
| 5,697,364 | * | 12/1997 | Chua et al. | 128/204.21 |
| 5,735,268 | * | 4/1998 | Chua et al. | 128/204.23 |

* cited by examiner

TRACHEAL GAS INSUFFLATION DELIVERY SYSTEM FOR RESPIRATION EQUIPMENT

BACKGROUND OF THE INVENTION

In respiratory treatment, a patient is connected to a ventilator that controls and/or supports the patient's breathing. The ventilator typically includes a means of mixing and forming a breathing gas having a predetermined ratio of one or more gases, the pressurized sources of which are connected to the ventilator. The ventilator could also possibly include internal means to compress ambient air. The gas mixture from the ventilator must contain sufficient amounts of oxygen for the treatment of the patient. For this reason, one of the gases is always $O_2$, or alternatively, in the extremely simplified case, the one single gas source is air. Other gases that are often mixed with $O_2$ are typically air ($N_2$ and $O_2$), and sometimes also helium.

To perform the mixing function, each of the gas flow paths has a regulating means, typically a valve, to regulate the gas flow. In the current state of the art technology, these regulators are driven by microprocessor control units according to information received by the controller from various pressure, flow, temperature and/or position sensors. The microprocessor compares this received information from the various sensors to predetermined control parameters and drives the regulators via feedback control. Mechanical mixers using flow resistance ratios are also used in some simple applications to supply a single flow controlling valve.

The patient is connected to the ventilator through a breathing circuit that includes an inspiratory limb, an expiratory limb, and a patient limb. These three limbs of the breathing circuit are connected together at a Y-piece connector. Breathing circuits are generally classified as either an open circuit or as a rebreathing circuit. An open breathing circuit is most often used in intensive care applications, whereas a rebreathing circuit is typically found in anesthesia systems. In both types of breathing circuits, the inspiratory limb conducts the gas to be inspired from the ventilator to the Y-piece connector. The expiratory limb conducts the expired gas from the Y-piece connector back to the ventilator. In an open circuit, the expiratory limb is connected to an expiratory valve that functions to regulate the expiratory pressure and discharges the gases to atmosphere. In a rebreathing circuit, the expiratory limb is connected to the ventilator for $CO_2$ removal.

In each type of breathing circuit, the patient limb connects the patient to the Y-piece connector and conducts inspired gases into the lungs and the expired gases back to the Y-piece connector. The patient limb typically includes an endotracheal tube, which is inserted into the trachea through the nose or mouth of the patient. Functionally, other equipment such as sensors, heat and moisture exchangers, and sampling connectors can be positioned between the Y-piece connector and the endotracheal tube.

When the patient is inspiring, the expiratory limb is closed through valves or other flow directing means depending on the breathing circuit. During inspiration, the ventilator forces the inspired gas to fill the patient's airways and lungs through the inspiratory and patient limbs with overpressure. During patient expiration, which is driven by the passive recoil of the lungs caused by the lungs' elastic force, the breathing circuit is arranged to conduct the exhaled gas through the patient and expiratory limbs back to the ventilator.

Modern ventilators used in intensive care applications use a base flow, which is a flow of gas supplied by the inspiratory valve to the inspiratory limb during the expiratory phase of the breathing cycle. The rationale behind the use of a base flow is to make it possible for the ventilator to detect an inspiratory effort by the patient with a minimal addition of extra work for the patient. In ordinary anesthetic rebreathing systems, fresh gas is delivered into the breathing system continuously from a fresh gas inlet.

The volume of breathing gas injected into the lungs during the inspiratory phase, also called the tidal volume ($V_t$), ranges from a few tens of milliliters for a newborn child up to more than one liter for a large adult. The rate at which the tidal volumes are delivered, called the respiration rate, varies from a few tens of breaths/min. down to a few breaths/min. depending on the patient size. The typical range of breathing gas volumes per minute varies according to body weight and condition, but typically ranges from less than 1 liter/min. up to more than 10 liters/min.

The inspiratory tidal volume ($V_t$) is normally delivered during the first third of the breathing cycle. Thus, the peak inspiratory flow may easily exceed thirty liters/min. and may momentarily reach more than 100 liters/min. in inspiration based on the control of a pre-set inspiratory pressure.

The tidal volume ($V_t$) that ventilates the patient's alveoli can be divided into two parts, an alveolar volume ($V_A$) and a deadspace volume ($V_D$). The alveolar volume ($V_A$) is defined as the volume of fresh gas that reaches the gas exchanging part of the patient's lung. In the alveoli, the high partial pressure of oxygen compared to the pressure of the perfused pulmonary blood flow makes the oxygen diffuse through the alveolar membrane and into the blood, such that the blood can transport the oxygen to tissues having a demand for oxygen. In an opposite manner, the high partial pressure of carbon dioxide ($CO_2$) in the perfused pulmonary blood flow, as compared to the low pressure of $CO_2$ in the fresh gas, makes the $CO_2$ diffuse through the alveolar membrane into the alveoli to be washed out in expiration.

The deadspace volume ($V_D$) is defined as the volume of fresh gas remaining in the patient limb and the upper airways of the patient, i.e., the trachea and bronchi at the end of inspiration. The deadspace volume does not take part in the gas exchange since it never reaches the patient's lungs.

Typically, the deadspace gas volume of a healthy human is in the order of 30% of the resting tidal volume, such as approximately 150 ml of deadspace in a 70 kg adult. In a patient with lung disease, the deadspace volume ($V_D$) can be significantly increased.

Figures 1A, 1B, 1C:
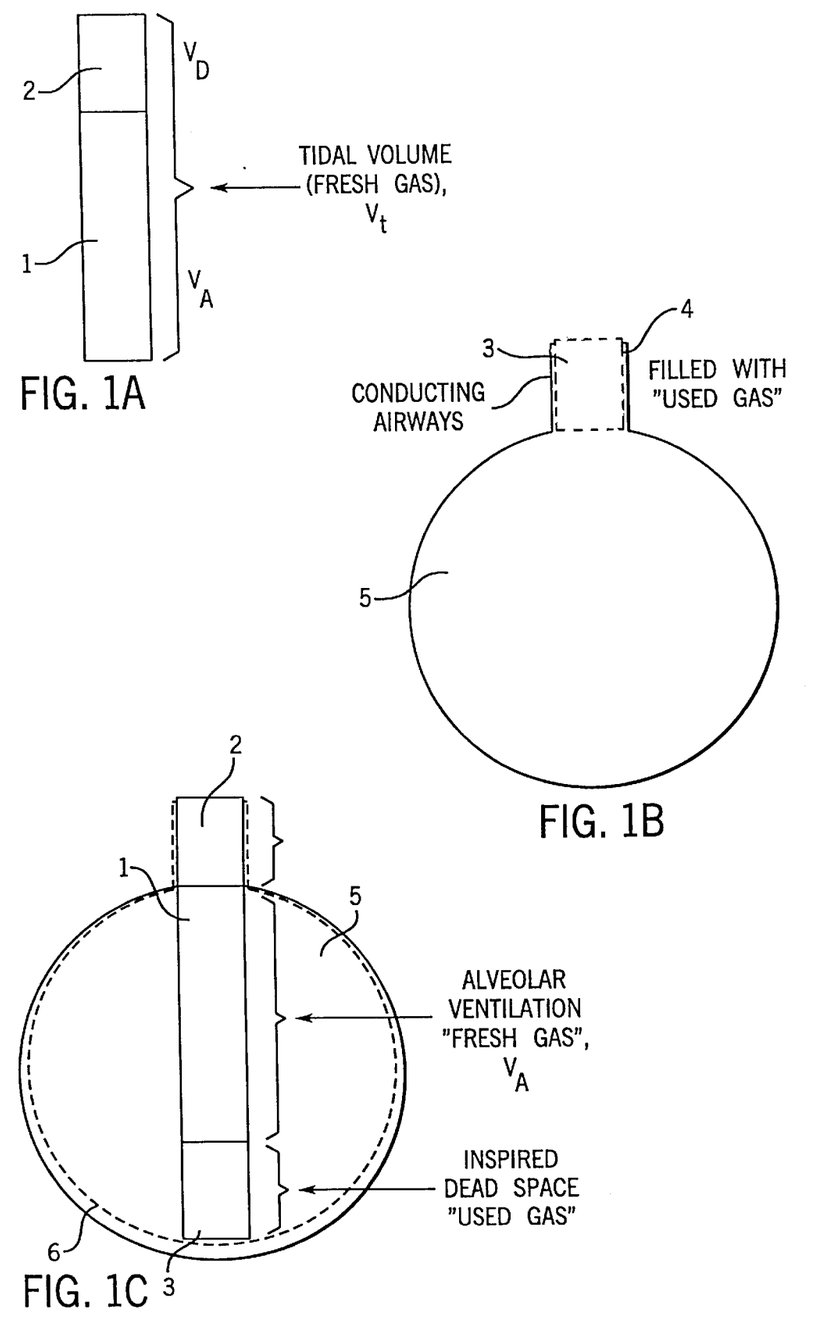
FIG. 1A is a schematic diagram illustrating the composition of the tidal volume of breathing gases.
FIG. 1b is a schematic diagram illustrating the volume and breathing gas condition of a patent's lung at the end of expiration.
FIG. 1c is a schematic showing the volume and breathing gas condition of a patient's lung at the end of inspiration.

The composition of the tidal volume ($V_t$) is clarified in FIG. 1, where FIG. 1A represents the tidal volume ($V_t$) divided into the alveolar volume ($V_A$) 1 and the deadspace volume ($V_D$) 2. Thus, the tidal volume is a simple sum of the alveolar 1 volume ($V_A$) 1 and the deadspace volume ($V_D$) 2. FIG. 1b diagrammatically represents the gas exchange situation within the lungs at the beginning of inspiration by the patient, after the exhalation flow has stopped. At this point in time, the upper airways and the patient limb forming a deadspace 4 are filled with exhaled gas 3. As shown in FIG. 1b, the gas volume remaining within the patient's lungs is represented by the reference numeral 5.

FIG. 1c shows the situation at the end of the inspiration by the patient. The volume of exhaled gas 3 previously present in the deadspace 4 has been sucked back into the patient's lungs 5, followed by the alveolar volume 1 of fresh inspiratory gas. The combination of the alveolar volume 1 and the exhaled gas 3 have increased the volume of the lungs by the amount designated by reference numeral 6. The deadspace comprised of the patient limb and the upper airways is now filled with fresh gas, referred to as the deadspace volume 2, which does not participate in the gas exchange within the lungs. Thus, the only volume participating in the gas exchange is the alveolar volume 1. Since the increase in lung volume is equal to the tidal volume ($V_t$), the volume of exhaled deadspace gas 3 is equal to the deadspace volume ($V_D$) 2.

The human body attempts to maintain a constant $CO_2$ partial pressure, $P_{ACO2}$, in the blood. Thus, a requirement exists for a certain amount of alveolar ventilation, see equation 1, which is determined by the patient's need for the $CO_2$ elimination necessary to maintain the constant $CO_2$ partial pressure, as set out in equation 2. The elimination of $CO_2$ cannot be significantly affected by increasing the concentration gradient, since the inspiratory $CO_2$ fraction is already close to zero. On the contrary, with the supply of more oxygen to the patient, the inspiratory oxygen fraction can be increased, which effectively increases the $O_2$ concentration gradient, the $O_2$ partial pressure, and thus decreases the $CO_2$ partial pressure.

$$\dot{V}_A = RR * V_A \quad \text{Equation (1)}$$

$$P_{ACO_2} \propto \frac{\dot{V}_{CO_2}}{\dot{V}_A} \quad \text{Equation (2)}$$

whereas:

$V_A$ = Alveolar volume  $\dot{V}_A$ = Alveolar ventilation $R$ = Respiration rate  $P_{ACO_2}$ = Alveolar $CO_2$ partial pressure $\dot{V}_{CO_2}$ = Body $CO_2$ production The pressure buildup in the lungs during ventilator assisted inspiration depends on lung mechanics characteristics and the delivered volume, as shown in equation 3. A high peak or average lung pressure affects the pulmonary blood perfusion in a negative way and may reduce the net amount of oxygen transported from the lungs to the tissue. Also, a high lung pressure may cause a rupture in the lung tissue, specifically when the tidal volume exceeds the lung elastic variation limits. Therefore, it is desirable to keep the alveolar pressure low so as to reduce the negative effect on the pulmonary blood flow and avoid possible lung damage. However, a certain pressure level is necessary to inject the needed tidal volume ($V_t$) into the lungs.

$$P_{MAX} \propto \frac{V_t}{C} \quad \text{Equation (3)}$$

whereas: C=Lung compliance

Based on the above discussion, it can be seen that the effectiveness of gas exchange, specifically the removal of $CO_2$, is defined by the alveolar volume ($V_A$) (equations 1 and 2), while the detrimental effects of ventilation are related to the increased pressure created by an increased tidal volume ($V_t$). The alveolar ventilation is determined by the gas exchange requirement and cannot be eliminated beyond a minimum without special and extremely expensive extracorporeal membrane oxygenation and carbon dioxide removal treatment. An alternative for improved effectiveness of the ventilation system is the reduction or preferably elimination of the deadspace volume ($V_D$), since the deadspace volume provides no gas exchange benefits to the patient.

Tracheal gas insufflation, abbreviated as TGI, is a method for the reduction of the deadspace volume ($V_D$) of exhaled gases. In the TGI method, the patient limb is flushed with fresh gas to reduce the amount of deadspace volume of exhaled gases. For this purpose, a special double lumen endotracheal tube is used to deliver the flushing gas flow at the distal end of the patient limb tube, thereby filling the patient limb tube with oxygen enriched gas having little to no carbon dioxide. During the next inspiration by the patient, the volume of exhaled gas pushed back into the lungs is greatly reduced. The tidal volume required to provide a desired alveolar volume ($V_A$) can be decreased correspondingly.

In many instances, the volume of the patient limb and upper airways can be as high as 100 ml. Typically, the tidal volume ($V_t$) is approximately 500 ml, so that the deadspace gas volume ($V_D$) represents approximately 20% of the tidal volume. By reducing the volume of exhaled gases in the deadspace volume, the maximum pressure set forth by equation 4 can be reduced, thereby reducing the negative effects caused by high lung pressure as described above.

As discussed above, reduction of the exhaled gases in the deadspace volume by expiratory flushing of the airway improves $CO_2$ elimination. A considerable body of experimental work in animals indicates the clinical potential of TGI in an intensive care setting. Although deadspace flushing is unlikely to be the only operative mechanism, the efficiency of TGI increases when the contribution of the TGI volume is proximal to the orifice of the flushing catheter to the total physiologic deadspace.

An important advantage in the reduction of the deadspace exhaled gas volume is the ability to reduce lung pressure while maintaining the required $CO_2$ elimination. When feeding TGI gas into the airway of the patient, some of the added gas will always be mixed with the patient gas distally of the TGI outlet, thus providing an efficient flush volume that can be greater than the actual volume proximal to the TGI outlet.

A comparison of continuously feeding a constant flow of oxygen and a pulsatile flow during the expiratory phase only into an outlet located in the distal end of the endotracheal tube was made in an article written by J. Marini entitled "Tracheal Gas Insufflation as an Adjunct to Ventilation". Although a continuous flow of oxygen gives a good deadspace wash, it has the drawback in that it adds to the maximum lung pressure unless compensated with ventilator adjustments. The pressure increases since the TGI flow is added to the inspiratory flow increasing the tidal volume with the previously mentioned detrimental effects. Additionally, since the device of the Marini article adds oxygen to the inspiratory flow, it will effect the actual oxygen fraction delivered to the patient. The result of the deadspace volume being filled with pure oxygen during expiration also adds to the uncertainty of the actual oxygen fraction delivered to the patient. Limiting the TGI flow selectively for the expiratory phase avoids the disadvantage of end-inspiratory overdistension.

A method for the delivery of the TGI is presented in WO 97/31670. In this reference, equipment is operated during the expiratory phase only. A further improvement on the ideas presented by Marini is the possibility of adjusting both the TGI flow rate and the TGI gas composition. This improvement is made possible by adding a dedicated mixer of oxygen and air with an adjustable needle valve for mixed gas flow rate adjustment to supply the gas for synchronizing TGI delivery apparatus. This apparatus receives the expiratory synchronization signal from the ventilator through a special signal line. The disadvantage of this system is the complexity and bulkiness for an already crowded intensive care environment. The device requires dedicated high pressure gas connection lines and mixers, and a separate adjustment for the gas mixture of the TGI to match the ventilator mixture. Additionally, the device shown in the above reference has to be customized with the make of the ventilator for the synchronization signal. One further problem of the described system arises from a patient safety standpoint. Since the system has its own high pressure supply connections, a risk of unintentional gas dosing exists, which results in overdistension of the patient's lungs. To eliminate this problem, separate pressure sensing and supervisory equipment are included in the described TGI dosing equipment.

SUMMARY OF THE INVENTION

The invention is directed to eliminating the problems of available TGI delivery devices. Specifically, it is an object of the present invention to provide a TGI delivery device that can deliver a TGI gas either continuously or intermittently in the expiratory phase. It is another object of the invention to provide such a device that can deliver TGI gas that automatically follows the gas mixture of a ventilator. It is another object of the invention to provide a TGI delivery device that is easy to use and has no additional high pressure gas connections. It is a further object of the present invention to provide a TGI delivery system that exhibits patient safety, is compact, and is compatible with a wide variety of currently available ventilators.

The present invention is a TGI system that takes advantage of the already existing ventilator gas mixture. Specifically, the gas used for TGI is drawn off from the fresh gas mixture in the inspiratory limb of the breathing circuit. This fresh gas mixture is drawn into the TGI system and is discharged through a TGI dosing line into the endotracheal tube, preferably near the distal end. A prerequisite for the functionality of this delivery system is a continuous fresh gas flow from the ventilator exceeding the TGI drawing capacity. In rebreathing circuits, this requirement will be inherent, because of the continuous fresh gas delivery and the unidirectional circulating gas scrubbed of the carbon dioxide during recirculation. In open circuits, the ventilator has to provide a base flow if the TGI system is arranged to draw during the expiration phase. Without the base flow, the TGI system would only draw the $CO_2$ enriched expiratory gas backward into the inspiratory limb, thereby negating the advantage of the TGI. If the TGI is arranged to draw during the inspiratory phase only, an intermediate storage vessel within the TGI delivery apparatus may be used.

The safety of the TGI apparatus of the present invention becomes obvious from the previous description. In the case of failing to the operative state, the TGI apparatus of the invention would only circulate the gas in a closed path defined by the patient limb-inspiratory limb-TGI suction line and TGI delivery line. When the suction capacity of the TGI apparatus is selected low compared to the ventilitory tidal volumes, the worst case failure to the inoperative state would be the loss advantage of the TGI.

The TGI apparatus according to the invention does not have any connections with the ventilator itself in the most simplified embodiment, although connection to the ventilator are possible in contemplated alternate embodiments. In the most simplified embodiment, the only connections are with the breathing circuit, which is universal as described above. These connections include a suctioning connection in the inspiratory limb and the dosing line connected to the endotracheal tube in the patient limb. Both of these connections can be small and flexible, such as 2–4 mm external diameter PVC tubes. A further connection to a power supply system to power the suction-dosing system is also required. The power supply system is preferably electrical.

To deliver the TGI gas synchronously with the expiratory phase of the respiration, a triggering mechanism is required. For this purpose, a flow sensor may be installed in the patient limb. This flow sensor will be used in detecting the flow direction, which can be used to determine the inspiratory and expiratory periods. When the sensor detects expiration, or some other triggering event in the patient breathing flow pattern, the TGI dosing is initiated. Furthermore, the same flow sensing element can be utilized to detect the start of inspiration to cease the TGI delivery. By having a flow sensor separate from the ventilator, the compatibility of the TGI apparatus with any modern ventilator is achieved, even with triggered TGI. Alternatively, a triggering signal, if available, can be supplied from the ventilator to the TGI delivery device.

The TGI delivery device, according to the invention, is compact in size since in the most simplified form it consists of only the pump, a suction line and a TGI dosing line. The compactness of the TGI delivery device of the invention is emphasized by the simple and small connections to the ventilating systems. The synchronization feature does not significantly increase the complexity of the TGI delivery device, since the equipment for triggering is often already available from the ventilator or from the patient monitoring equipment

BRIEF DESCRIPTION OF THE DRAWINGS

The drawings illustrate the best mode presently contemplated of carrying out the invention.

In the drawings.

DETAILED DESCRIPTION OF THE INVENTION

Figure 2:
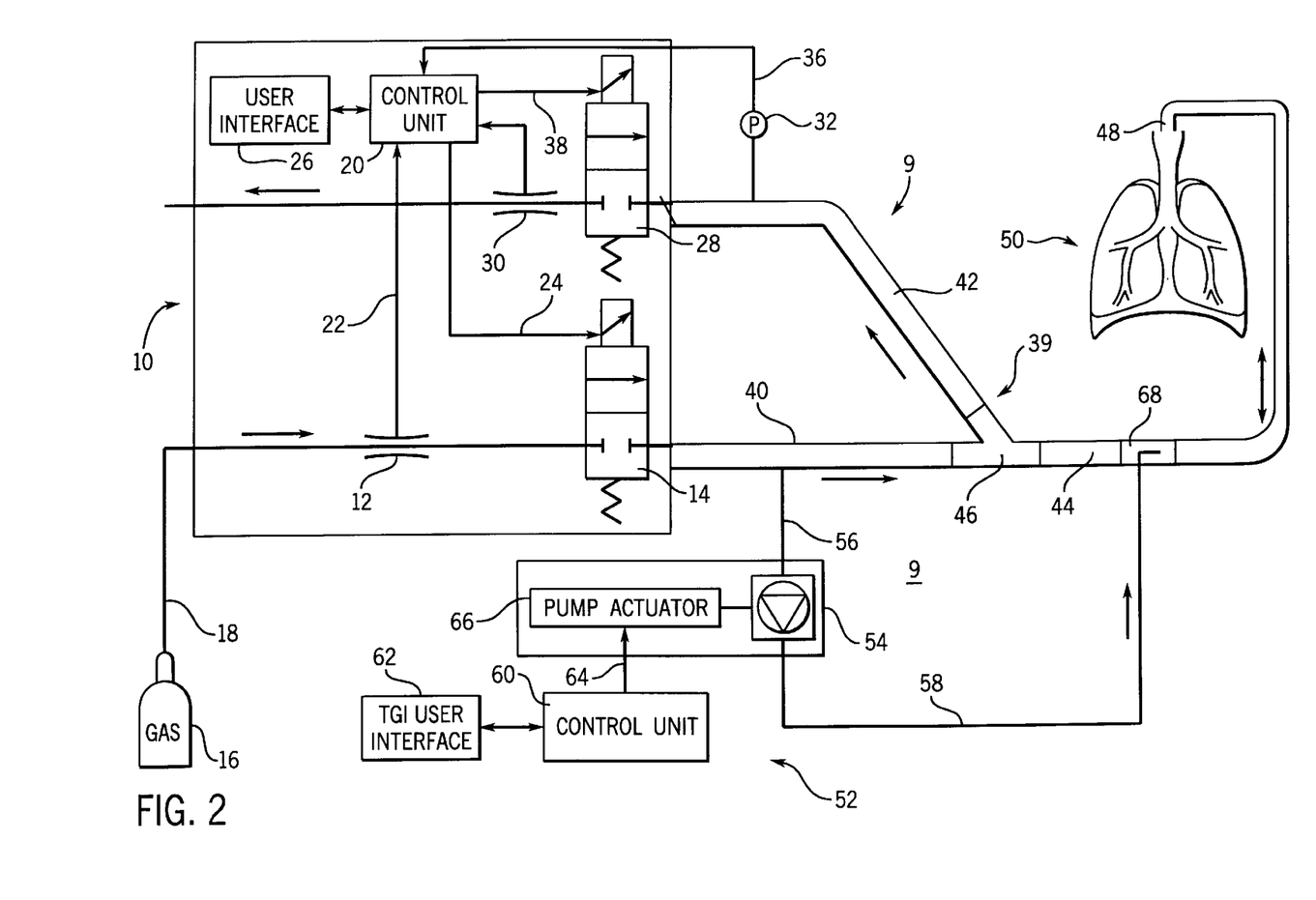
FIG. 2 is a schematic view showing the TGI apparatus of the invention.
Figure 3:
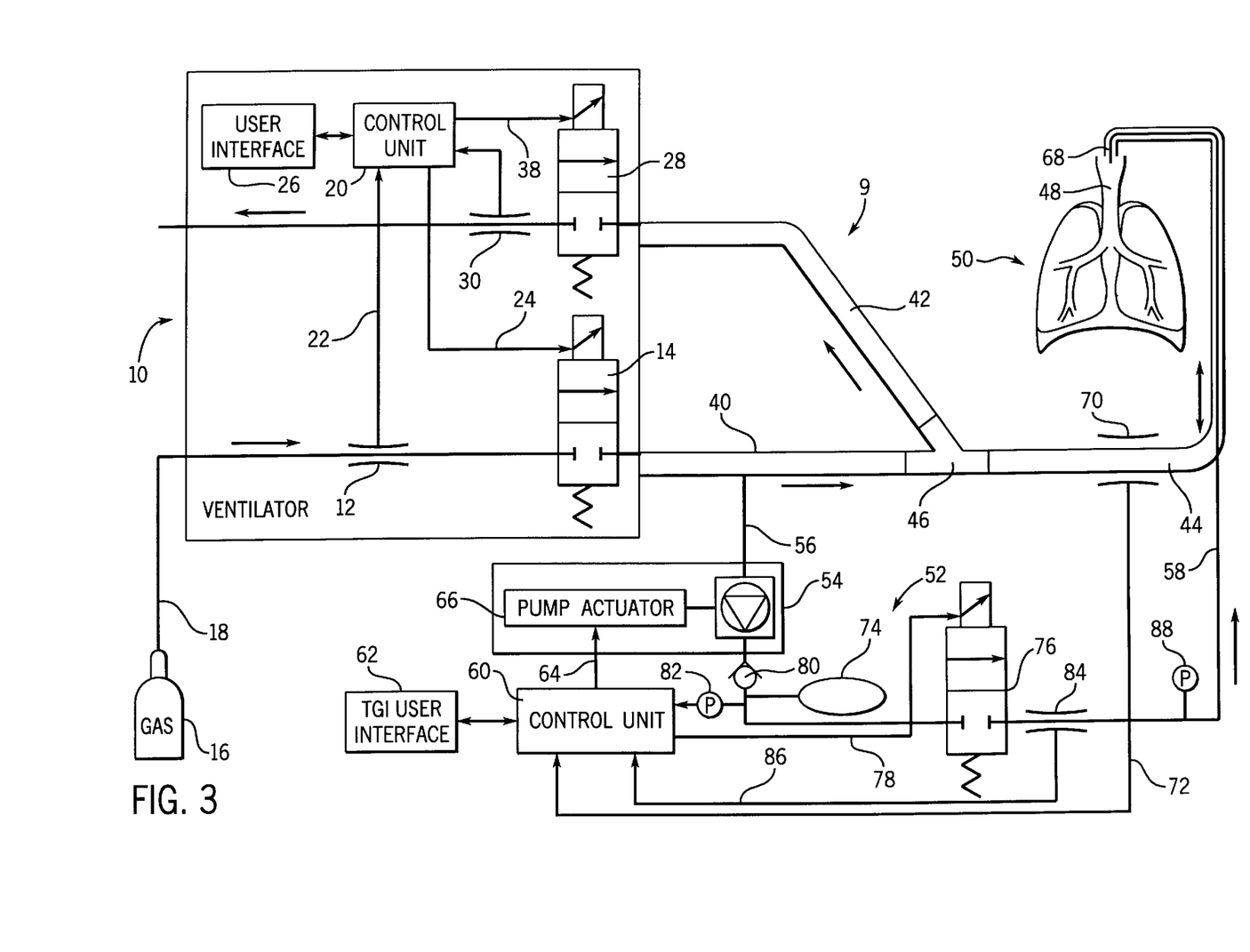
FIG. 3 is a schematic view showing a first alternate apparatus of the invention.

The first two embodiments of the invention, shown in FIGS. 2 and 3 respectively, represent a TGI delivery system 9 of the invention in connection with an open breathing circuit. The TGI delivery system 9 is suitable for use with a conventional ventilator 10 used to ventilate a patient's lungs by simulating the spontaneous breathing volumes and frequencies. The ventilator 10 has an inspiration delivery system including a flow sensor 12 and a flow control valve 14. The flow sensor 12 and the flow control valve 14 are connected to a pressurized gas source 16 through a high-pressure gas line 18. The flow sensor 12 communicates with a ventilator control unit 20 through a flow signal line 22. The control unit 20 controls the flow control valve 14 through a control line 24. The control unit 20 controls the flow control valve 14 in a manner such that the flow pattern of the ventilator 10, as measured by the flow sensor 12, matches a series of user defined values preset through a user interface 26.

The ventilator 10 also has an expiration control system including an expiration valve 28, a flow sensor 30, a pressure sensor 32, a flow signal line 34, a pressure signal line 36, and an expiration valve control line 38. The expiration valve 28 is controlled according to the information measured from the flow sensor 30 and the pressure sensor 32 in a manner to match the preset values input through the user interface 26.

A breathing circuit 39, which is separate from the ventilator 10, generally includes an inspiratory limb 40, an expiratory limb 42, a patient limb 44 and a Y-piece connector 46. The patient limb 44 terminates in the patient's upper airways 48, as by an endotracheal tube 68, thereby forming a conduit between the ventilator 10 and the patient's lungs 50.

The breathing circuit 39 is also coupled to a tracheal gas insufflation (TGI) delivery system 52. TGI delivery system 52 includes a TGI flow generator 54, an inlet line 56, and a delivery line 58. A TGI control unit 60 is in communication with the TGI flow generator 54 to control its operation. In its simplest form, the TGI control unit 60 only provides a signal to power the TGI flow generator 54, while a TGI user interface 62, in its simplest form, acts only as an on-off switch. The TGI flow generator 54 is a device that is able to generate flow through the inlet line 56 and the delivery line 58. It is contemplated that the TGI flow generator 54 could be selected from a variety of types of pumps or fans, as long as the TGI flow generator 54 is able to generate the required flow through the inlet line 56 and the delivery line 58.

In operation, the TGI flow generator 54 is activated through a control line 64 extending between the control unit 60 and a pump actuator 66. When operated, the TGI flow generator 54 suctions or draws off gas through the inlet line 56 from the inspiratory limb 40 and supplies the gas through the delivery line 58 into the patient limb 44. Preferably, the delivery line 58 provides gas into the distal end of endotracheal tube 68 in the patient limb 44. Although the delivery line 58 is shown connected to the patient limb 44, it should be understood that the delivery line 58 could be connected to the Y-piece connector 46 and transmitted within the patient limb 44 down to the dosing point, which could be anywhere in the patient limb 44 or even in the upper airways 48.

The supply of gas contained in the delivery line 58 is delivered into the patient limb 44 until the patient begins inspiration to reduce the amount of exhaled gas deadspace volume. Upon inspiration, the supply of gas is inhaled into the patient's lungs. Alternatively, if the delivery line 58 extends into the patient's upper airways or lungs (see FIG. 3), the supply of gas is delivered immediately upon the cessation of exhalation.

The embodiment shown in FIG. 2 is a continuous flow TGI delivery system. In order to modify this continuous flow TGI delivery system into an intermittent, triggered embodiment, synchronization means need to be added. As shown in FIG. 3, the necessary synchronization can be derived from a separate patient flow sensing element 70 and a signaling line 72 extending between a breathing gas sensing element 70 and the TGI control unit 60. The synchronization signal could also be received through a signal line from the ventilator control unit 20, if such a signal is available. For example, the signal in control line 24 may be employed to enable TGI delivery system 52 when inspiration valve 24 is closed.

In operation, when the synchronizing signal attains the triggering condition, TGI delivery is initiated. Possible synchronizing start events include the start of expiration, the end of inspiration, expiration flow falling below a predefined level, an elapsed amount of time from beginning of expiration, or exhalation of a preset expired volume. A natural synchronizing stop event for the TGI delivery system is the start of inspiration. The TGI user interface 62 is modified in order to permit the input of the required synchronizing parameters.

In the synchronized form of the TGI delivery system shown in FIG. 3, the delivery takes place only during about one third of the breathing cycle. In order to get enough volume in the TGI delivery within this relatively short period of time, the TGI flow generating unit 52 may be arranged to pressurize an intermediate cylinder 74 that is connected to the delivery line 58 as shown in FIG. 3. The volume of the intermediate cylinder 74 is advantageously 0.5–3 dl. To facilitate TGI delivery, the delivery line 58 is also equipped with a flow control valve 76 that is controlled by the control unit 60 through a control line 78. The flow control valve 76 may be either a digitally controlled on-off type or a proportionally controllable valve for various flow rates. In the embodiment shown in FIG. 3, the TGI flow generator 54 may run either continuously or intermittently. When running intermittently, the flow path from the intermediate cylinder 74 backwards through the TGI flow generator 54 to inlet line 56, is equipped with a check valve 80 to prevent the back flow of gas from the intermediate cylinder 74. Although the check valve 80 is shown as a separate component, such check valves 80 are often an inherent feature found in many pumps, which can be advantageously used. In the embodiment shown in FIG. 3, the control unit 60 also has the capability to control the flow control valve 76 through the control line 78.

The delivery line 58 upstream from the flow control valve 76 may also be equipped with a pressure sensor 82. The pressure measured by the pressure sensor 82 reflects the pressure of intermediate cylinder 74 and may be used by the control unit 60 for controlling the cylinder loading. By regulating the system pressure, the TGI delivery flow, and thus the volume of gas delivered, can be regulated. If the TGI flow generator 54 ceases loading the intermediate cylinder 74 for the dosing period, the TGI flow and delivered volume can be deduced from the intermediate cylinder volume and the pressure difference occurring under the dosing.

The delivery line 58 may also be equipped with a flow sensor 84 for the TGI flow measurement. The flow sensor 84 is coupled to the control unit 60 through a data line 86. When the flow control valve 76 is a proportional valve, the flow sensor 84 can be utilized to regulate the TGI to a predefined flow rate. The plurality of sensors and devices in communication with the control unit 60 add to the functionality of the control unit 60 and possibly to the TGI user interface 62 in the form of different possible informational displays.

In the embodiment of the breathing system shown in FIG. 3, a pressure sensor 88 is positioned downstream from the flow control valve 76. When little or no flow is present in the delivery line 58, the pressure measured by the sensor 88 equals the pressure at the outlet of the delivery line 58. When the outlet of the delivery line is located in the distal end of the endotracheal tube 68, as in FIG. 2, the measured pressure at sensor 88 is approximately the airway pressure. A problem with conventional airway pressure measurement has been occlusion of the pressure measuring tube in the airway due to patient excretions, like mucus and moisture. In the TGI delivery system shown in FIG. 3, this problem is avoided since the delivery line 58 is flushed open with the TGI gas dose. TGI delivery system 52 thus provides a convenient, reliable way to obtain airway pressure measurement. Ventilators 10 of current manufacturer typically by a special operation sequence stop the exhalation flow for measurement of the airway pressure.

In the embodiments shown in FIG. 2 and 3, a ventilator expiratory base flow is required if the TGI flow generating unit 54 suctions during the expiratory phase of the breathing cycle.

Figure 4:
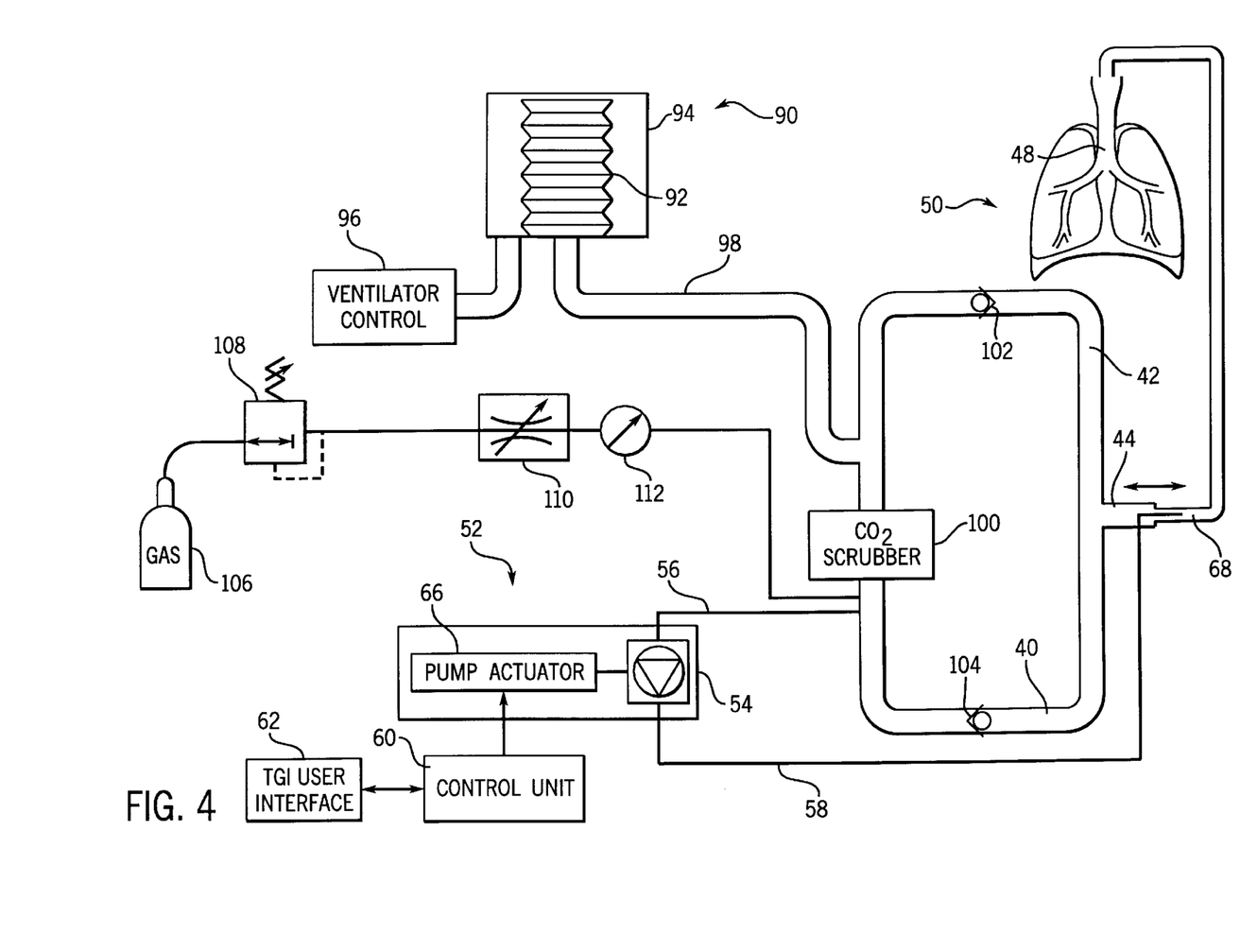
FIG. 4 is a schematic view showing a second alternative apparatus of the invention.

Referring now to FIG. 4, thereshown is a third embodiment of the present invention for a rebreathing system. The system shown in FIG. 4 includes a ventilator 90 having the form of a bellows in a housing. Inside bellows 92 is the gas to be respired. A pair of check valves 102 and 104 are positioned within the circuit to direct the gas flow within the circulating path between the bellows 92 and the housing 94. A driving gas controlled by a ventilator control unit 96. When the ventilator control unit 96 pressurizes the housing 94 by adding gas, the bellows 92 will contract and the gas within the bellows 92 will flow through a ventilator conduit 98, a $CO_2$ scrubber 100, an inspiratory limb 40 and a patient limb 44 into the lungs 50.

Expiration begins when the ventilator control unit 96 relieves the pressure within the bottle 94. The elasticity of the lungs 50 make the gas flow out of the lungs, through the patient limb 44, into the expiratory limb 42 and the ventilator conduit 98 back into the bellows 92. The circulating gas is supplied with additional fresh gas, as needed, from the gas supply 106 through a pressure regulator 108, a flow regulator 110 and a flow measurement unit 112 and typically into the inspiratory limb 40 of the rebreathing circuit.

A TGI system inlet line 56 is connected between the $CO_2$ scrubber 100 and an inspiratory check valve 104. Regardless of whether the TGI system 52 is suctioning during inspiration or expiration, the gas at the suctioning site is free of $CO_2$ and represents the inspired gas mixture. The check valves 102 and 104 prevent back flow of expired gas into the inspiratory limb when suctioning during expiration, such that no additional base flow is required.

It is recognized that other equivalents, alternatives, and modifications aside from those expressly stated, are possible and within the scope of the appended claims.

We claim:

1. A tracheal gas insulation delivery system for use with a breathing system including a ventilator for supplying a breathing gas to a breathing circuit, the breathing circuit having an inspiratory limb coupled to a patient limb for forming, with the patient's upper airway, a breathing path for the patient's lungs, the tracheal gas insufflation delivery system comprising:

a flow generator (54) having an inlet and an outlet;
an inlet line (56) having a first end connectable to the inspiratory limb of the breathing circuit and a second end connected to the inlet of the flow generator, the flow generator being operable to draw off a supply of gas from the inspiratory limb through the inlet line; and
a delivery line (58) having a first end connected to the outlet of the flow generator and a second end positioned to deliver the supply of gas at a desired point along the breathing path of the patient for flushing the breathing path with the supply of gas.

2. The tracheal gas insufflation delivery system of claim 1 wherein the flow generator includes a pump.

3. The tracheal gas insufflation delivery system of claim 1 wherein the flow generator includes a fan.

4. The tracheal gas insulation delivery system of claim 1 further comprising a control unit (60) coupled to the flow generator, the control unit operating the flow generator to control the delivery of the supply of gas to the breathing path.

5. The tracheal gas insulation delivery system of claim 4 further comprising a user interface (62) in communication with the control unit, the user interface being operable to input operating variables related to the operation of the tracheal gas insufflation delivery system into the control unit.

6. The tracheal gas insufflation delivery system of claim 4 wherein the control unit operates the flow generator to deliver the supply of gas to the patient upon detection of a triggering condition, wherein the supply of gas is delivered until the detection of a stop event.

7. The tracheal gas insufflation delivery system of claim 4 wherein the control unit operates the flow generator to deliver the supply of gas to the patient when the expiratory gas flow from the patient has dropped below a predetermined threshold and until the detection of inspiratory flow to the patient.

8. The tracheal gas insufflation delivery system of claim 1 wherein the flow generator is continuously operable.

9. The tracheal gas insufflation deliver system of claim 1 wherein the flow generator is intermittently operable.

10. The tracheal gas insufflation delivery system of claim 1 wherein when the patient limb includes an endotracheal tube, the connection between the delivery line and the patient limb is located in the endotracheal tube.

11. The tracheal gas insufflation delivery system of claim 1 wherein the second end of the delivery line is connectable to the patient limb.

12. The tracheal gas insufflation delivery system of claim 1 further comprising a flow sensor (84) positioned in the delivery line, the flow sensor generating a signal corresponding to the flow of gas in the delivery line.

13. The tracheal gas insufflation delivery system of claim 1 further comprising:

a flow control valve (76) positioned between the flow generator and the delivery line to control the flow of the supply gas from the flow generator to the delivery line; and
a control unit (60 coupled to the flow generator for controlling the flow generator and wherein the flow control valve is controlled by the control unit.

14. The tracheal gas insufflation delivery system of claim 1 further comprising a flow sensor (70) positionable in the patient limb, the flow sensor indicating the timing and flow of gas within the patient limb.

15. The tracheal gas insufflation delivery system of claim 1 further comprising:

an intermediate storage cylinder (74) in fluid communication with the outlet of said flow generator, the storage cylinder being pressurized to increase the amount of the supply of gas delivered to the patient through the delivery line; and
a flow control valve (76) positioned in the delivery line downstream of said storage cylinder to control the flow of the supply of gas from the flow generator to the delivery line.

16. The tracheal gas insufflation delivery system of claim 13 further including a control unit (60) coupled to the flow generator for controlling the flow generator, and wherein the flow control valve is controlled by the control unit.

17. The tracheal gas insufflation delivery system of claim 15 further comprising a check valve (80) positioned between the intermediate cylinder and the flow generator to prevent gas flow from the intermediate cylinder to the flow generator.

18. The tracheal gas insufflation delivery system of claim 15 further comprising a flow sensor (84) positioned in the delivery line, the flow sensor generating a signal corresponding to the flow of gas in the delivery line.

19. The tracheal gas insufflation delivery system of claim 15 further comprising a pressure sensor (88) positioned downstream from the flow control valve in pressure connection with the delivery line, the pressure sensor measuring the pressure within the patient limb when the flow within the delivery line is minimal.

20. A tracheal gas insufflation delivery system for use with a ventilitory breathing system, the ventilitory breathing system including a ventilator and a breathing circuit, the breathing circuit having an inspiratory limb in connection with a patient limb to conduct inspiration gas from the ventilator into the patient's lungs, the tracheal gas insufflation system comprising:

a flow generator (54) having an inlet and an outlet;

an inlet line (56) having a first end connectable to the inspiratory limb of the breathing circuit and a second end connected to the inlet of the flow generator, the flow generator being operable to suction a supply of gas from the inspiratory limb through the inlet line;

a delivery line (58) having a first end connected to the outlet of the flow generator and a second end positioned to deliver the supply of gas to the patient;

a flow control valve (76) positioned between the flow generator and the delivery line to control the flow of the supply of gas from the flow generator to the delivery line;

an intermediate storage cylinder (74) positioned between the flow generator and the flow rate valve, the storage cylinder being pressurized by the flow generator to increase the pressure of the supply of gas delivered to the patient through the delivery line;

a first flow sensor (70) positionable in the patient limb, the first flow sensor indicating the timing and directional flow of gas within the patient limb; and a control unit (60) in communication with the flow generator, the first flow sensor, and the flow control valve to control the delivery of the supply of gas to the patient for tracheal gas insufflation.

21. The tracheal gas insufflation delivery system of claim 20 further comprising a user interface (62) in communication with the control unit, the user interface being operable to input operating variables into the control unit.

22. The tracheal gas insufflation delivery system of claim 20 wherein the first flow sensor generates a signal indicating the inspiration and expiration of breathing gases by the patient, such that the control unit operates the flow control valve to deliver the supply of gas used for tracheal gas insufflation during the expiration of breathing gases by the patient.

23. The tracheal gas insufflation delivery system of claim 20 further comprising a check valve (80) positioned between the intermediate cylinder and the flow generator to prevent gas flow from the intermediate cylinder to the flow generator.

24. The tracheal gas insufflation delivery system of claim 20 further comprising a second flow sensor (84) positioned between the flow control valve and the delivery line, the second flow sensor generating a signal corresponding to the flow of gas delivered by the flow generator.

25. The tracheal gas insufflation delivery system of claim 20 further comprising a pressure sensor (88) positioned between the flow control valve and the delivery line, the pressure sensor measuring the pressure within the patient limb when the flow generator is deactivated.

26. A tracheal gas insufflation delivery system for use with a ventilitory breathing system, the ventilitory breathing system including a ventilator and a breathing circuit, the breathing circuit having an inspiratory limb in connection with a patient limb to conduct inspiration gas from the ventilator into the patient's lungs, the tracheal gas insufflation system comprising:

a flow generator (54) having an inlet and an outlet;

an inlet line (56) having a first end connected to the inlet of the flow generator and a second end connectable to the inspiratory limb of the breathing circuit, the flow generator being operable to suction a supply of gas from the inspiratory limb through the inlet line;

a delivery line (58) having a first end connected to the outlet of the flow generator and a second end positioned to deliver the supply of gas to the patient;

a flow control valve (76) positioned between the flow generator and the delivery line to control the flow of the supply of gas from the flow generator to the delivery line;

an intermediate storage cylinder (74) positioned between the flow generator and the flow control valve, the storage cylinder being pressurized by the flow generator to increase the amount of the supply of gas delivered to the patient through the delivery line; and a control unit (60) in communication with the flow generator, the ventilator, and the flow control valve, the control unit being coupled to the ventilator to receive information related to the patient breathing from the ventilator such that the control unit operates to control the delivery of the supply of gas to the patient for tracheal gas insufflation.

27. The tracheal gas insufflation delivery system of claim 26 further comprising a user interface (62) in communication with the control unit, the user interface being operable to input operating variables into the control unit.

28. The tracheal gas insufflation delivery system of claim 26 further comprising a check valve (80) positioned between the intermediate cylinder and the flow generator to prevent gas flow from the intermediate cylinder to the flow generator.

29. The tracheal gas insufflation delivery system of claim 26 further comprising a flow sensor (84) positioned between the flow control valve and the delivery line, the flow sensor generating a signal corresponding to the flow of gas delivered by the flow generator.

30. The tracheal gas insufflation delivery system of claim 26 further comprising a pressure sensor (88) positioned between the flow control valve and the delivery line, the pressure sensor measuring the pressure within the patient limb when the flow generator is deactivated.

* * * * *

UNITED STATES PATENT AND TRADEMARK OFFICE
CERTIFICATE OF CORRECTION

PATENT NO. : 6,196,222 B1
DATED : March 6, 2001
INVENTOR(S) : Erkki Heinonen et al.

It is certified that error appears in the above-identified patent and that said Letters Patent is hereby corrected as shown below:

Column 9,
Line 50, delete "insulation" and substitute therefor -- insufflation --;
Line 50, delete "deliver" and substitute therefor -- delivery --;

Column 10,
Line 9, delete "insulation" and substitute therefor -- insufflation --.

Signed and Sealed this

Tenth Day of December, 2002

JAMES E. ROGAN
*Director of the United States Patent and Trademark Office*